United States Patent
Taurel

(10) Patent No.: US 9,314,401 B2
(45) Date of Patent: Apr. 19, 2016

(54) TITRATION PACKAGE

(75) Inventor: Diego M. Arbaiza Taurel, Frankfurt am Main (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 1567 days.

(21) Appl. No.: 12/735,572

(22) PCT Filed: Jan. 14, 2009

(86) PCT No.: PCT/EP2009/000174
§ 371 (c)(1),
(2), (4) Date: Oct. 19, 2010

(87) PCT Pub. No.: WO2009/095154
PCT Pub. Date: Aug. 6, 2009

(65) Prior Publication Data
US 2011/0039942 A1    Feb. 17, 2011

Related U.S. Application Data

(60) Provisional application No. 61/062,603, filed on Jan. 28, 2008.

(30) Foreign Application Priority Data

Jan. 28, 2008 (EP) ................................. 08001546

(51) Int. Cl.
| | |
|---|---|
| *B65D 71/00* | (2006.01) |
| *A61K 31/13* | (2006.01) |
| *A61J 1/03* | (2006.01) |
| *A61J 7/04* | (2006.01) |
| *A61P 25/28* | (2006.01) |
| *A61B 17/00* | (2006.01) |

(52) U.S. Cl.
CPC . *A61J 1/03* (2013.01); *A61J 7/0481* (2013.01)

(58) Field of Classification Search
CPC ........ A61K 31/13; A61P 28/28; A61B 17/00; B65D 71/00; A61J 1/03; A61J 7/0481
See application file for complete search history.

(56) References Cited

U.S. PATENT DOCUMENTS

| | | |
|---|---|---|
| 3,381,808 A | 5/1968 | McGraw et al. |
| 4,706,815 A | 11/1987 | Curtis et al. |
| 4,736,849 A | 4/1988 | Leonard et al. |
| 4,958,736 A | 9/1990 | Urheim |
| 5,788,974 A | 8/1998 | D'Amico et al. |
| 6,273,260 B1 | 8/2001 | ColDepietro et al. |
| 2005/0011804 A1 | 1/2005 | Zanden et al. |
| 2007/0163918 A1* | 7/2007 | Klatt et al. ..................... 206/531 |
| 2008/0000798 A1* | 1/2008 | Gutmann et al. ............. 206/532 |
| 2009/0038981 A1 | 2/2009 | Leifeld |

FOREIGN PATENT DOCUMENTS

| | | |
|---|---|---|
| EP | 1293436 | 3/2003 |
| GB | EP 0852208 | 6/1996 |
| JP | 200170404 | 3/2001 |
| JP | 3117622 | 12/2005 |
| JP | 2007-531541 | 11/2007 |
| WO | WO2004087038 | 10/2004 |
| WO | WO 2005009326 | 2/2005 |

OTHER PUBLICATIONS

European Search Roport for EP 08001546 of Jun. 10, 2008.
International Preliminary Report on Patentability for PCT/EP2009/000174 of May 4, 2010.
International Search Roport for PCT/EP2009/000174 of Mar. 23, 2009 with Written Opinion.
Japanese Office Action for JP2010-543418 of Sep. 4, 2013.

* cited by examiner

*Primary Examiner* — Sarah Pihonak
*Assistant Examiner* — Jason A Deck
(74) *Attorney, Agent, or Firm* — Hueschen and Sage

(57) ABSTRACT

The present invention relates to a titration package for providing at least one pharmaceutical composition in at least two different dosages. The titration package comprises at least two sets. Each set comprises at least three individually addressable regions. Each addressable region preferably comprises or is represented by a pharmaceutical composition, preferably a tablet. The dosage of the pharmaceutical composition is the same within each of the at least two sets ("common dosage"), while the dosages of the pharmaceutical compositions are different for one of the at least two sets compared to at least one other of the at least two sets. The arrangement of the at least two sets is not a matrix-like arrangement.

25 Claims, 5 Drawing Sheets

TITRATION PACKAGE

The present invention relates to a titration package for providing at least one pharmaceutical composition in at least two different dosages.

The titration package comprises at least two sets. Each set comprises at least three individually addressable regions. Each addressable region preferably comprises or is represented by a pharmaceutical composition, preferably a tablet.

The dosage of the pharmaceutical composition is the same within each of the at least two sets ("common dosage"), while the dosages of the pharmaceutical compositions are different for one of the at least two sets compared to at least one other of the at least two sets.

Within each set, the at least three individually addressable regions are preferably arranged essentially along a horizontal line (defining a "row") or are arranged essentially along a vertical line (defining a "column").

In one embodiment of the present invention, the respective distances between the centers of two immediately adjacent individually addressable regions within one set, preferably within all sets, said set(s) comprising at least three individually addressable regions, for example the distance between region 1 and region 2, or the distance between region 2 and region 3 respectively, are smaller by at least 10%, preferably by at least 20%, further preferably by at least 50%, further preferably by at least 100%, further preferably by at least 200%, further preferably by at least 500%, than the distance between the center of each of said at least three immediately adjacent individually addressable regions (region 1, region 2 and region 3) of at least one set, respectively, on the one hand, and the corresponding three immediately adjacent individually addressable regions (region 1', region 2' and region 3') of all other sets of the package.

In equivalent terms, that are meant to supplement or replace the disclosure given in the previous paragraph, the present invention relates to an arrangement of at least two sets, each set comprising at least three addressable regions, wherein said arrangement of sets is not a matrix-like arrangement.

Therein, a "matrix-like" arrangement is commonly mathematically defined as follows for example for two sets of three addressable regions each, respectively: [(1,1), (1,2), (1,3); (2,1), (2,2), (2,3)] or [(1,1), (1,2); (2,1), (2,2); (3,1), (3,2)] or, more generally for n sets; each set having m members, [(1,1), (1,2), . . . , (1,n); (2,1), (2,2), (2,n); . . . ; (m,1), (m, 2), (m,n)] with n and m being integers running from 2 to infinity and the first coordinate in parenthesis being the x-coordinate of a Cartesian coordinate system and the second coordinate being the y-coordinate. In a matrix-like arrangement, each member can be identified by giving one x-coordinate and one y-coordinate. For unambiguous identification of each member in this matrix-like arrangement, it suffices to label (indicate) each row and each column.

Titration or compliance packages having a matrix-type arrangement are principally known from the prior art.

For example, WO 2005/009326 describes a titration package for enabling compliance with a regimen of changing dosage of medication over a period of time. The compliance package comprises a backing having an array of receivers. Said array is made of a plurality of columns and a plurality of rows. A plurality of sets of tablets are provided in the receivers. Each tablet in a set has a common dose of medication and a different dose than a tablet of a different set. Each set of tablets is disposed in receivers of an adjacent row or an adjacent column. Indicia are provided and disposed adjacent the columns and rows for displaying common days and successive weeks. This specific positioning of indicia is specifically tied to the disclosed matrix-like setup.

EP 852 208 ("EP '208") discloses a container for administering a gradually increasing amount of a medicament which is used for the treatment of Parkinson's disease or the like. In order to achieve this technical object, EP '208 provides 2 tablet container for housing tablets which are arranged in a matrix form with the vertical columns designating the date and the horizontal designating several occasion of any given day, for example "breakfast", "lunch" and "dinner".

U.S. Pat. No. 4,958,736 contemplates a package for the sequential daily oral administration of pharmacologically active contraceptive tablets comprising a carrier sheet provided with 28 compartments arranged in four substantially parallel rows of seven substantially parallel columns. Three adjacent rows have an active tablet in each compartment. A fourth row has a placebo tablet in each compartment. A line of severability is provided between the row of placebo tablets and an adjacent row of active tablets to enhance removal of the row of placebo tablets from the remainder of the package.

U.S. Pat. No. 5,788,974 ("US '974") describes a compliance pack for treating heliobacteria *pylori* induced infections. For this, US '974 suggest a compliance pack in matrix-form having days ranging from "1" to "7" on the y-axis and "breakfast", "lunch", "dinner" on the x-axis. The pack is an elongated rectangular container in the form of a blister pack comprising of a base with the above-mentioned day chart along the y-axis, to aid the patient in cutting with scissors, or along a perforation so as to separate doses, one day at a time. The patient could then carry an entire day's dose with them wherever they go, thus greatly facilitating and enhancing compliance, as the size of the overall box could be quite cumbersome.

While the highly symmetric matrix-like arrangement of tablets as described in the art may be an efficient way to arrange a given number of tablets on a given substrate, accidental miss-dosing due to "slipping" from one row or column into an adjacent row or column must be seen as problem, in particular if the patient's senses are impaired. This "slipping" is particularly worrisome if different dosages are present in adjacent rows or columns as is the case for titration packages.

In light of the prior art, one object according to the present invention is to provide a titration package that further minimizes or avoids accidental miss-dosing.

A further objective is to provide a titration package that is particularly suited for older patients, patients with diminished eyesight or other diminished cognitive capabilities, or blind patients, or patients with diminished or decreasing memory function.

The above-given objectives, along with other objectives, are solved by the titration package of claim 1.

The arrangement of sets, in particular of rows and/or columns, and of individually addressable regions within these sets as claimed in claim 1 ensures or enables that individual pharmaceutical compositions, in particular tablets (associated with the above-referenced individually addressable regions of each row and/or column) belonging to different dosage regimes (for example different weeks) are clearly separated from each other thus avoiding or at least minimizing an accidental "slipping" from one row (column) to an immediately adjacent row (column), as is the case in a matrix-like arrangement as known from the prior art.

A strictly geometric and highly symmetric arrangement as represented by a matrix or a table induces the accidental crossing-over from one row/column into an adjacent row/column. This holds in particular for patients whose reliance on abstract or geometric comprehension may be impaired due to age, illness, impaired eyesight, mental dysfunction or the like.

The present invention breaks up the strict geometry and symmetry of the matrices known from the art and provides an arrangement of sets that are not only sufficiently spaced from one another but also differentiated in position thus providing support for memorizing the position of the most recently used blister cavity (in case the addressable regions are defined by blister cavities comprising a tablet).

In the following, preferred embodiments of the present invention are disclosed in more detail.

In accordance with the present invention, a "titration package" is meant to be any substrate, container or packaging that allows to provide at least two different dosages (doses) of one or more pharmaceutical composition(s).

Providing two (chemically) different pharmaceutical compositions (in particular in regard to the active ingredients thereof) in formally the same amount within one titration package is also within the scope of "providing two different dosages".

In a preferred embodiment according to the present invention, the titration package comprises two or more different doses/dosages of one pharmaceutical composition, wherein the chemical nature of the active ingredient is the same for the at least two different dosages, while the amount of active ingredient varies between the two different dosages.

According to a preferred embodiment, the purpose of a titration package is to allow for an up- and/or down-titration of the dosage of at least one pharmaceutical composition, preferably until a certain final dotage level is reached. Titration packages are also known as "compliance packages" as they aid the patient in complying with the therapeutically indicated dosage regime.

The term "package" is only meant to be limiting in the sense that the package must be able to contain and/or affix the pharmaceutical composition as provided in any conceivable form at individually addressable regions that are part of the package. The "addressable regions" should be identifiable by the user of the package.

In accordance with the present invention, a "pharmaceutical composition" preferably is any chemical element, chemical compound, composition, mixture or material that is used or may be used to treat any conceivable illness, disease, (medical) condition. Pharmaceutical compositions may include/comprise food supplements, nutritional supplements or other supplements or agents provided for affecting any conceivable bodily or mental function of humans or animals.

Placebos are also included as pharmaceutical compositions. Therefore, the present invention also covers a titration package comprising at least one set with an active ingredient and at least one second set with placebos.

In accordance with the present invention, the pharmaceutical composition is preferably a solid. The pharmaceutical composition in solid form is further preferably provided as at least one member selected from the following group: tablets, pills, troches, lozenges, suppositories, capsules, (fine) granules, pellets or beads. Any of these pharmaceutical compositions can be coated or uncoated and may have any conceivable shape, wherein the shape preferably is or resembles a circle, an ellipsoid, a polygonal shape and/or is "bone" shaped.

Preferably the pharmaceutical composition is provided as a tablet.

In accordance with the present invention, the term "dosage" is to be understood to mean the absolute amount of at least one active ingredient of a pharmaceutical composition, for example given in units of "milligram", "gram", "$LD_{50}$" or the like.

In accordance with the present invention, the dosage of the pharmaceutical composition is the same within each of at least two sets, while the dosages of the pharmaceutical compositions are different for one of the at least two sets compared to at least one other of the at least two sets.

The at least two different dosages provided in at least two different sets preferably differ by at least 10%, further preferably by at least 20%, further preferably by at least 50% and further preferably by at least 100%.

In a preferred embodiment, three or more different dosages are provided, in three or more different sets, further preferably four or more different dosages in four or more different sets.

It is preferred that the at least two sets all comprise pharmaceutical compositions; that are of the same dosage within each set but of a different dosage between the sets, preferably between four different sets, further preferably in 5 mg, 10 mg, 15 mg and 20 mg doses, respectively, each dose being a ±50% by weight.

In one embodiment, it is preferred that the three or more of four or more dosages each differ by at least 50%, further preferred by at least 100%, for example 5 mg, 10 mg, 20 mg, 40 mg.

In one embodiment, it is preferred that the increments in dosage difference between the three or more of four or more dosages are the same, respectively. Preferably the increment is 5 mg or 10 mg (±50%), for example 5 mg, 10 mg, 15 mg, 20 mg.

In the context of the present invention, a "set" means any arrangement of three or more addressable regions of any type as arranged on a two or three-dimensional substrate.

The at least two sets according to the present invention are preferably physically separated from each other and discernible as belonging to different dosage regimes.

It is particularly preferred that the at least two sets are present as foldable flaps arranged along one edge of a polygonal central area, preferably a square central area (see FIG. 1).

This arrangement ensures that different sets representing different dosages are spaced apart sufficiently so that accidental crossing over from one set into another is avoided or minimized. Also, since the flaps are foldable, they can be advantageously folded onto the central area thus saving space in the folded stage of the packaging, while providing a convenient and easily accessible display of the sets in the unfolded stage.

Therein, it is particularly preferred that the flaps, once folded onto the central area, do not protrude over the two-dimensional projection of said central area. Further preferably, the pharmaceutical compositions of each set are provided in blister packages/compartments representing or being part of the addressable regions.

In another embodiment, it is preferred that the at least two sets are present as at least two individual sub-packages, preferably as polyhedral or polygonal boxes, further preferably as rectangular or square boxes (parallelepipeds), foldably connected to each other by at least one hinge per two packages ("train" of sub-packages; see FIGS. 5 and 6).

Therein, said boxes preferably comprise the pharmaceutical compositions, preferably as pills, troches, suppositories, tablets, capsules or the like, preferably embedded in said box and representing the addressable regions. Further preferably, the addressable regions are blister packages comprising the tablets, capsules or the like.

In a preferred embodiment according to the present invention, two different sets are discernible from one another by at least one means selected from the following group, or any combination or two or more elements thereof: different imprints on or adjacent to different sets; different coloring and/or shading of the sets, or of parts thereof, different color, imprint, shape or size of the pharmaceutical components that are part of the set, preferably tablets, pills, troches, lozenges and the like, pictograms on or near each set; different size, different materials, different shape of the sets.

In the context of the present invention, an "addressable region" is understood to mean any region on a two- or three-dimensional substrate that is part of a set and can be reproducibly differentiated from any other addressable region by a user of the titration package. Preferably, two adjacent addressable regions within a set and/or between two sets are physically separated from each other, i.e. do not overlap and, further preferably, do not touch each other.

In accordance with the present invention, no limitations exist as to how two different addressable regions are made addressable/identifiable. In a preferred embodiment, addressable regions are differentiated from each other by at least one means selected from the following group, or any combination thereof: highlighting by color and/or shading and/or imprint, provision of a blister pack at the position of the addressable region the blister pack then being the addressable region; provision of an indentation/elevation; provision of a different material or a gradient in material, provision of a pouch or other conceivable (sub-)containment for a pharmaceutical composition.

In accordance with the present invention, the addressable regions may also be defined by the pharmaceutical compositions as such, preferably solids, further preferably pills, capsules, tablets, lozenges or troches, that are directly or indirectly attached to or adhered to the package or parts thereof. It is also conceivable that individual addressable regions of a set do not comprise a pharmaceutical composition ("blank").

No principal limitations exist in regard to the number of sets and the number of addressable regions thereon. The titration package according to the present invention preferably comprises at least two sets of at least three individually addressable regions, respectively. Preferably the at least two sets are at least two rows or at least two columns, or at least one row and at least one column.

It is further preferred, that the titration package comprises at least four sets, each set having at least four, five, six, seven, eight, nine, ten or more or twenty or more addressable regions, respectively.

According to the present invention, the titration package may also comprise at least three, five, six, seven, eight, nine or ten sets. Each of these sets preferably has at least four, five, six, seven, eight, nine, ten, twenty or more addressable regions, respectively.

It is preferred that four sets are provided, each having more than five, preferably seven or more, addressable regions each comprising at least one pharmaceutical composition, preferably in the form of a tablet, pill, lozenge, capsule, granule, suppository, troche or the like, wherein the four sets all comprise pharmaceutical compositions that are of the same dosage within each set but of a different dosage between the four different sets.

In accordance with the present invention, at least two sets may also have different numbers of addressable regions as long as each set has at least three addressable regions. For example, one set may have five addressable regions, while the next set, for example, may have ten addressable regions.

In a particularly preferred embodiment of the present invention, the respective (geometric) distances between at least two, preferably between all centers of two immediately adjacent individually addressable regions within one set, said set comprising at least three individually addressable regions (region 1, region 2 and region 3), for example the distance between region 1 and region 2, as well as the distance between region 2 and region 3, respectively, are smaller by at least 10%, preferably by at least 20%, further preferably by at least 50%, further preferably by at least 100%, further preferably by at least 200%, further preferably at least 500%, than the distance between the center of each of said at least three immediately adjacent individually addressable regions (region 1, region 2 and region 3) of at least one set, respectively, on the one hand, and the corresponding three immediately adjacent individually addressable regions (region 1', region 2' and region 3') of all other sets of the package.

Therein, "corresponding" means that the positioning of the addressable regions in the two different sets that are compared must be the same or as similar as possible. For example, if the first set has seven members and the first three members are considered, then, in a second set also having seven members, the first three members must be considered as well. For example, in FIG. 1, the distance between "Day 1" and "Day 2" of "Week 1" is much smaller than the distance between "Day 1 " of "Week 1" and corresponding "Day 8" of "Week 2".

Therein "(geometric) distance" means the distance as measured from the geometric center of one addressable region to the geometric center of the other addressable region.

For example, if a package comprises four sets, each set having seven addressable regions (each region being represented by one blister package), the distance between any two immediately adjacent regions, for example from the geometric center of the first blister to the geometric center of the second blister (in the same set), may be, for example 1 cm, whereas the distance between the geometric centers of the respective first blisters of two different sets is 5 cm.

In the symmetric matrix-type arrangement of the prior art, at least the distances between adjacent regions within one set and the distances between regions of two adjacent sets will always be the same, or similar, thus contributing to the similarity of regions and the potential for confusion between different addressable regions.

Preferably, the different sets are realized as individual "rows" and "columns", wherein each row and each column, respectively, comprises at least three individually addressable regions (region 1, region 2 and region 3, for example) that are arranged essentially along a horizontal line, in case of a row, or are arranged essentially along a vertical line, in case of a column.

In accordance with the present invention, the term "row" is understood to mean any arrangement of three or more, preferably five or more, further preferably 7 or more, further preferably 10 or more addressable regions on a substrate, wherein the regions are essentially arranged along a horizontal line (assuming that the row is seen in top view and the standard coordinate system is applied). It is within the scope of the present invention if addressable regions of the row are shifted, staggered, offset or slightly displaced relative to each other, as long as the overall assembly of addressable regions essentially follows such a horizontal pattern.

In accordance with the present invention, the term "column" is understood to mean any arrangement of three or more, preferably five or more, further preferably 7 or more, further preferably 10 or more addressable regions on a substrate, wherein the regions are essentially arranged along a vertical line (assuming that the row is seen in top view and the standard coordinate system is applied). It is within the scope of the present invention if addressable regions of the column are shifted, staggered, offset or slightly displaced relative to each other, as long as the overall assembly of addressable regions essentially follows such a vertical pattern.

In a preferred embodiment, the fact that the dosages are different between at least two sets is indicated by at least one of the following, or a combination of two or more of the following: imprinting the dosage or any other differentiating feature onto or next to each addressable region and/or on any solid pharmaceutical compound associated therewith; imprinting the dosage or any other differentiating feature next to a set, or part thereof, of addressable regions, color-coding each or some addressable region(s) of a given set and/or color-coding each or some solid pharmaceutical compound associated therewith; associating different dosages with differing shapes of the addressable regions and/or the solid pharmaceutical compounds associated therewith, providing a highlighting bar of different color and/or different shading encompassing two or more addressable regions of one set; providing different blister packages for different sets; providing embossed printing (Braille) indicating the dosis or any other differentiating feature for different sets.

In a preferred embodiment, indicia are provided next to each addressable region and/or next to each pharmaceutical composition (the pharmaceutical composition optionally being the addressable region). Further preferably, these indicia are consecutive days ranging from "1" at least "7", further preferably from "1" at least "28".

By using consecutive numbers for the days, supported by the non-matrix-like (i.e. not highly symmetric) geometric arrangement of the tablets, confusion of days/tablets is minimized or avoided.

In a preferred embodiment, each set comprises seven members and the number of the week is indicated next to each set, for example "Week 1", "Week 2" etc.

In another preferred embodiment, the dose is indicated next to each set, for example "5 mg", "10 mg" etc.

Both (number of week and dosage) may be imprinted next to the sets.

In a preferred embodiment the pharmaceutical composition is a medicament for treating Alzheimer's. Further preferably, the pharmaceutical composition is or comprises memantine (hydrochloride).

The present invention also relates to a kit comprising the titration package according to any one of the embodiments described above, memantine or memantine hydrochloride and instructions for treating Alzheimer's. Memantine is a medicament that is preferably titrated up from 5 mg to 20 mg in 5 mg increments. Since the patients taking memantine are typically somewhat visually and/or mentally impaired, the highly symmetric non-matrix-like arrangement of sets according to the present invention is particularly suitable for the intended use.

EXAMPLES

In the following, two examples are given how a titration package in accordance with the present invention can be realized.

In a first example as shown in FIGS. 1 to 4, the titration package comprises two physically separate entities, in the following referred to as "cover" and "insert". The cover is not shown in the Figure. The outside cover preferably is a sleeve that slides over the insert (1) and essentially fits therewith, i.e. the outer dimensions of the insert as folded are essentially the same as the inner dimensions of the cover. The insert (1) may also be presented without a cover.

Figure 3:
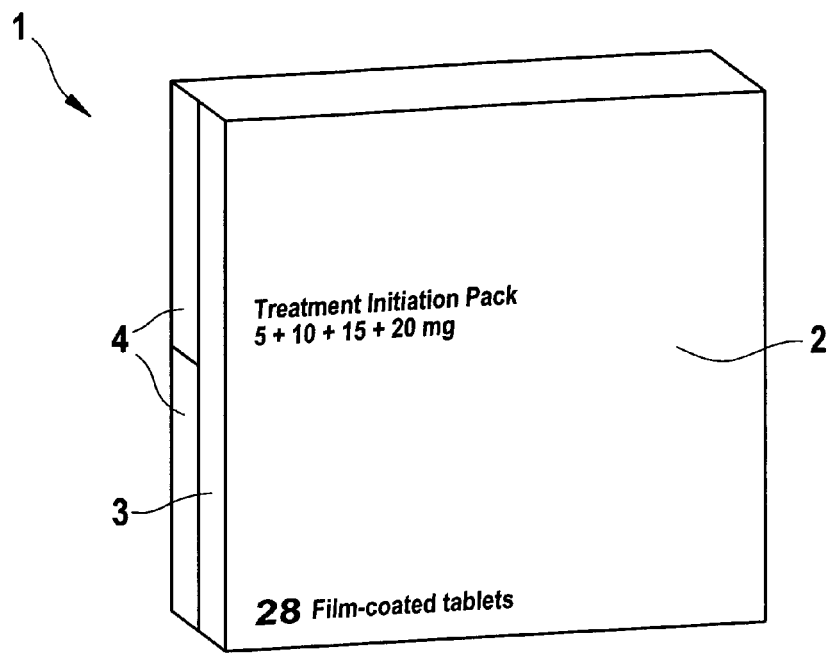
FIG. 3 An insert (1) where once folded, the flaps lie perpendicular to each other, one set of two (4) on top of the other set of two (3), thus completely covering the centre square (2) without protruding the same.
Figure 4:
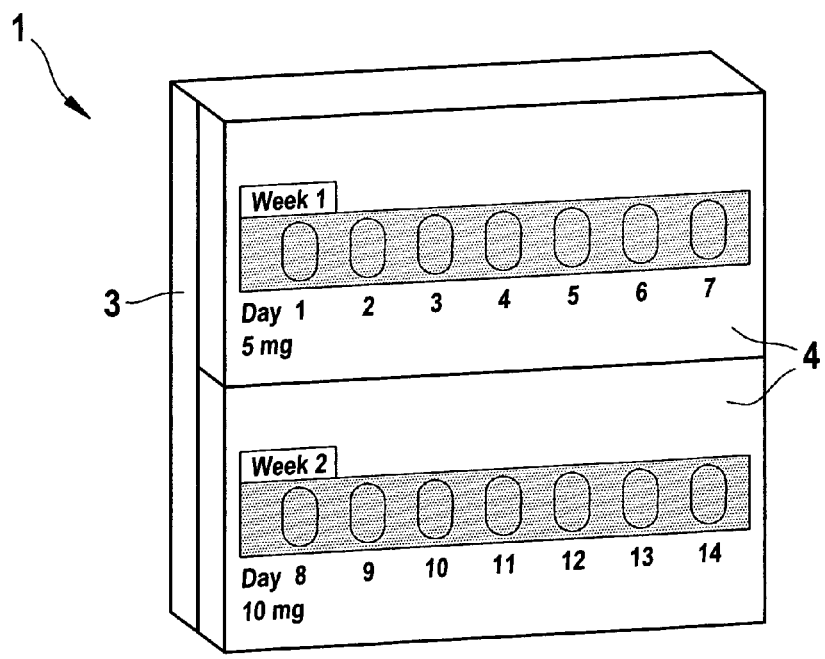
FIG. 4 An insert (1) where once folded, the flaps lie perpendicular to each other, one set of two (4) or top of the other set of two (3), thus completely covering the centre square (2) without protruding the same.

The insert (1) is (completely) contained inside the cover when the insert is completely folded and the titration package is properly closed (see FIG. 3).

In the closed stage, a kit comprising the package and the tablets in differing doses may further comprise instructions on a separate leaflet, wherein the leaflet is slipped in the space between cover and insert. The leaflet may also be (partly) attached to either the insert (1) or the cover.

Figure 1:
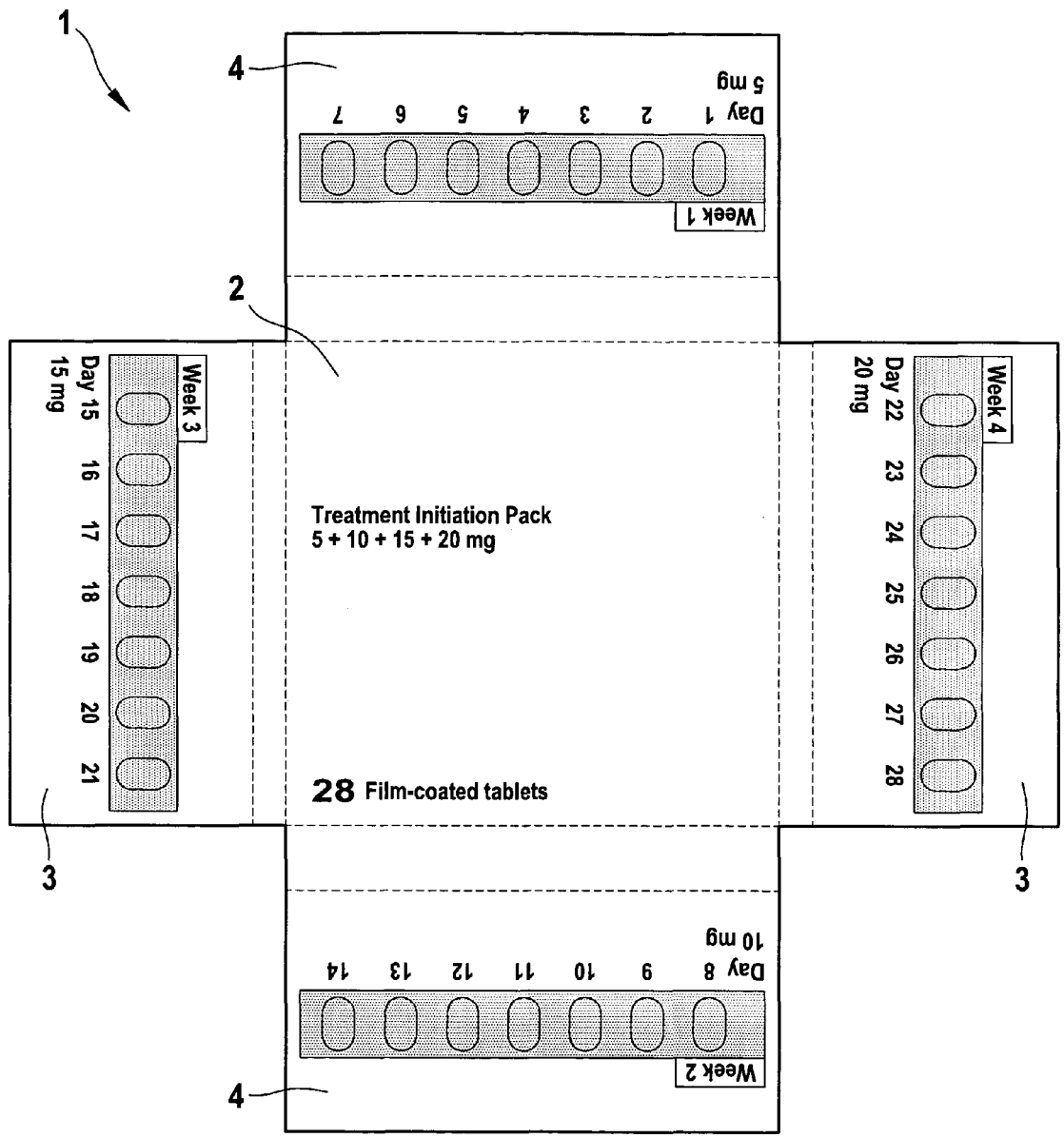
FIG. 1 The completely unfolded state of the insert (1), the four flaps (3) and (4) are attached to the square (2) and extend along the length of each of the four outer sides (edges) of the square.

As shown in FIG. 1, the insert (1) consists of a flat central area (2) in the shape of a "square". Four rectangular areas (in the following referred to as "flaps") (3) and (4) are attached to the four outer edges of said central flat area. In accordance with a preferred embodiment of the present invention, the square is made of a plasticized cardboard material. The square as such comprises no further parts, in particular no blister cavities. However, it is preferred that product information is imprinted onto this area.

Figure 2:
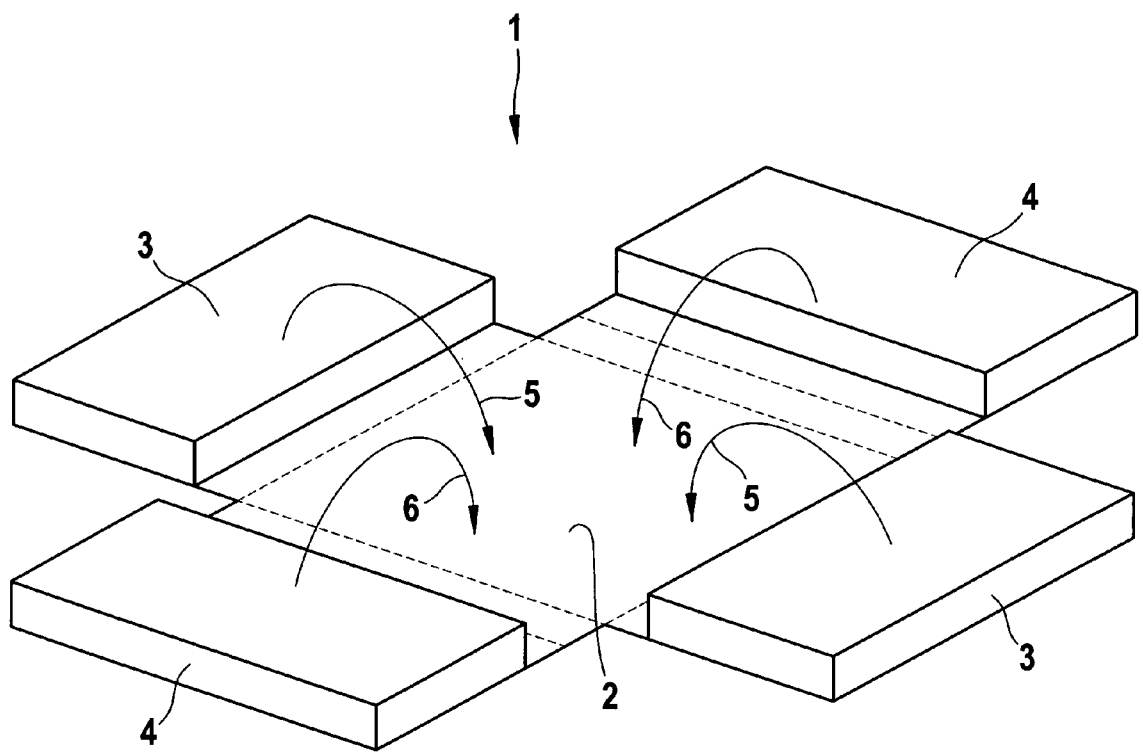
FIG. 2 The completely unfolded state of the insert (1), the four flaps (3) and (4) are attached to the square (2) and extend along the length of each ot the our outer sides (edges) of the square. As shown, Flaps (3) are folded in first in movement (5) while flaps (4) are folded on top of flaps (3) in movement (6).

In the completely unfolded state of the insert (1) as shown in FIGS. 1 and 2, the four flaps (3) and (4) are attached to the square (2) and extend along the length of each of the four outer sides (edges) of the square. The flaps are preferably made of a double layer of the same material as the square. The flaps comprise the blister cavities for holding the tablets as described in more detail below.

All flaps (3), (4) can be folded along a first pre-folded edge (being the above-mentioned outer edge of the square). Two Opposing flaps (4) comprise a second edge inside the flap area that is also pre-folded. This staggering of the distances between the edges of the two sets of opposite flaps allows to fold the flaps while accommodating the blisters that typically have a thickness of several mm (see FIG. 2). As shown in FIG. 2, flaps (3) are folded in first in movement (5) while flaps (4) are folded on top of flaps (3) in movement (6). Once folded, the flaps lie perpendicular to each other, one set of two (4) on top of the other set of two (3), thus completely covering the centre square (2) without protruding the same (see FIGS. 3 and 4).

Each flap comprises a "row" or "column" (which line of blisters is seen as a "row" and which is seen as a "column" depends on how the insert is oriented) of more than two, for example seven, blister cavities, respectively (see FIG. 1). Each "row" or "column" of blisters is located approximately halfway between the first pre-folded edge (forming the edge with the square) and the outer edge of the flap. Each "row" or "column" is preferably essentially symmetric in respect to its sideways (lengthwise) positioning, i.e. is essentially equally close to the two sides of the flap.

In the unfolded stage (FIGS. 1 and 2) of the insert, the "rows" and "columns" are not in contact with each other and are clearly separated from each other. In particular, in the unfolded stage the rows and columns are not arranged in a matrix, i.e. elements (blister cavities) of different rows and columns have no direct (x,y) relationship with each other. In the folded stage, the rows and columns lie on top of each other (see FIG. 4).

Preferably, the insert is labeled as follows: Each flap containing the row/column of seven blisters comprises one label printed onto each flap indicating the number of the week (ranging from "Week 1" to "Week 4").

Preferably, consecutive weeks are arranged on adjacent flaps (i.e. the flap of "Week 1" is immediately adjacent to the flaps of "Week 2" and "Week 4", while "Week 3" is located opposite on the other side of the square.

Alternatively, consecutive weeks are arranged in pairs opposite to each other (i.e. the flap of "Week 1" is immediately adjacent to the flaps of "Week 3" and "Week 4", respectively, while "Week 2" is located opposite on the other side of the square.

This illustrates a general concept of the present invention according to which sets of dosages that follow each other are spaced apart as much as (geometrically) possible.

Each row of blisters (one week) is positioned on a background bar that is colored, wherein the coloring is preferably a darker shade of grey/blue the higher the close (i.e. grey for Week 1 and dark blue for Week 4). Each flap also comprises one set of seven indicia ranging from day "1" to "28" next to each blister to indicate successive days of the four weeks. In particular, one flap has blisters labeled "Day 1, 2, 3, 4, 5, 6, 7", the next flap has blisters labeled "Day 8, 9, 10, 11, 12, 13, 14" and so on (see FIG. 1). The afore-described labeling is preferably present on the inner and on the outer side of the flap (see FIGS. 1 and 4).

According to the present invention, the individual labeling of each blister (containing a tablet) is advantageous since the rows and columns are not arranged in a matrix thus not allowing to unambiguously address or identify an individual member (certain day of a certain week) by simply giving an (x,y)-coordinate. This arrangement is associated with the advantage that different weeks corresponding to different dosages are clearly separated from each other, and that an accidental "slipping" from one row (column) to an immediately adjacent row (column), as is the case in a matrix-like arrangement, is minimized or altogether avoided.

Furthermore and preferably, the outside of each flap is labeled in the lower left corner of the outside of each flap with a value for the respective dose of Memantine hydrochloride, in this case, exemplarily, 5 mg, 10 mg, 15 mg, and 20 mg.

Figure 5:
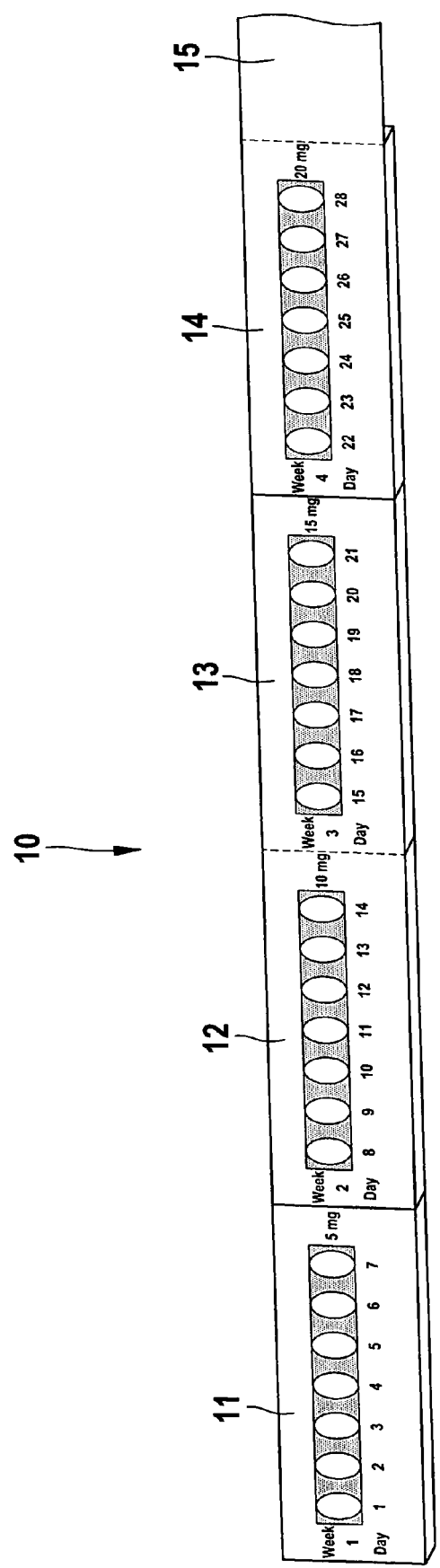
FIG. 5 A fully extended insert (10) which essentially consists of a "train" of two or more (here: four) foldable compartments (11)-(14), i.e. rectangular boxes comprising, in this case, seven blister cavities per box. The compartments are connected by hinge-type joints (15).
Figure 6:
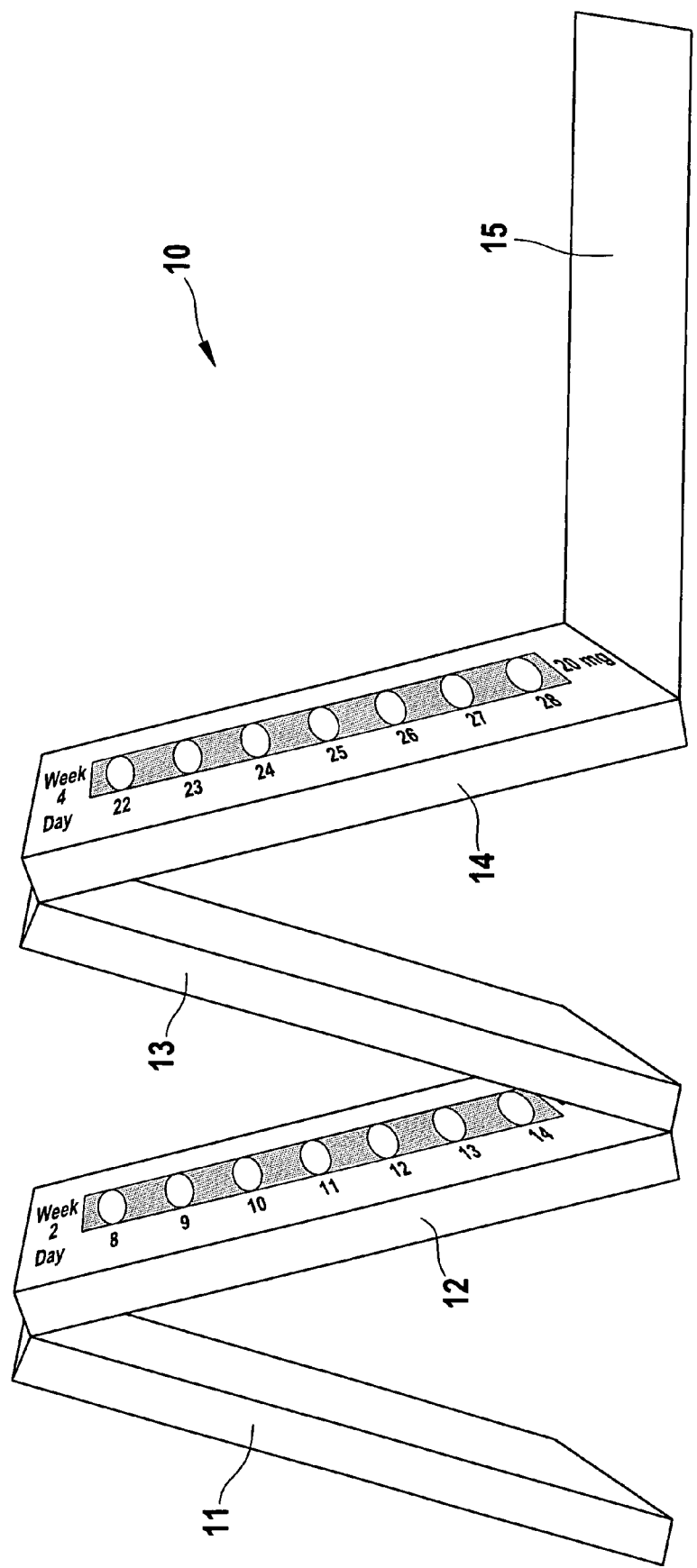
FIG. 6 An insert (10) which essentially consists of a "train" of two or more (here: four) foldable compartments (ll)-(14), i.e. rectangular boxes comprising, in this case, seven blister cavities per box. The compartments are connected by hinge-type joints (15).

In a second example as shown in FIGS. 5 and 6, the insert (10) essentially consists of a "train" of two or more (here: four) foldable compartments (11)-(14), i.e. rectangular boxes comprising, in this case, seven blister cavities per box. The compartments are connected by hinge-type joints (15), for example made of a flexible paper-like material.

The compartments/boxes (11) to (14) of the train have dimensions comparable to the flaps (3) and (4) discussed in the previous example.

Most importantly, the four compartments (boxes) form a "train" of compartments, i.e. the first compartment is foldably connected to the second compartment, the second compartment is foldably connected to the third compartment and the third compartment is foldably connected to the fourth compartment (see FIGS. 5 and 6).

In the fully extended state (FIG. 5), the four compartments are lying flush next to each other bringing the seven blister cavities of each compartment (11) to (14), respectively, in alignment to formally give the appearance of one single row of 28 blisters. However, the spacing between the last blister of one row ("set") of one compartment (11), (13) and the first blister of the next row ("set") of the next compartment (12), (14) is greater than the spacing in between blisters for both adjacent compartments, respectively.

In the fully folded state, the four boxes/compartments are lying one on top of the other forming a rectangular box of the same length and width as the individual compartment.

In an intermediate stage, due to the flexible connection ("hinge") between two adjacent compartments, the four boxes/compartments form the shape of an "M" in various degrees of compression or extension (see FIG. 6). Optionally, attached leaflet (15) may provide relevant information.

In regard to labeling, each compartment is labeled to show the week (ranging from "Week 1" to "Week 4"), the dose (being 5 mg, 10 mg, 15 mg, 20 mg for each of the four consecutive rows (or "sets") respectively) and the day of the week. The day of the week is labeled for each blister in each row individually, i.e. in the first compartment, blisters 1 through 7 are labeled day "1" to "7". The same applies for the other three compartments, respectively.

Furthermore, the increasing dosage between the (here: four) sets is indicated by a background coloring bar underlining the seven blisters, the intensity of which increases from the leftmost ("Week 1") compartment to the rightmost compartment ("Week 4").

The invention claimed is:
1. A titration package for providing a pharmaceutical composition in at least two different dosages,
   wherein the package comprises at least two sets,
   wherein each set comprises at least three individually addressable regions, wherein an addressable region is any region on a two or three-dimensional substrate that is part of a set and can be reproducibly differentiated from any other addressable region by a user of the titration package and wherein two adjacent addressable regions within a set and between two sets are physically separated from each other,
   wherein each addressable region comprises or is represented by a pharmaceutical composition,
   wherein the dosage of the pharmaceutical composition is the same within each of at least two sets, while the dosages of the pharmaceutical compositions are different for one of the at least two sets compared to at least one other of the at least two sets,
   wherein the respective distances between all centers of immediately adjacent individually addressable regions within each set, respectively, are smaller by at least 20% than the distance between the center of each of the at least three immediately adjacent individually addressable regions of all other sets of the package, wherein the at least three individually addressable regions of one set are arranged essentially along a horizontal line, defining a row, and the at least three individually addressable regions at least one other set are arranged essentially along a vertical line, defining a column.

2. The titration package of claim 1, wherein the respective distances between all centers of two immediately adjacent individually addressable regions within each set, respectively, are smaller by at least 50% than the distance between the center of each of said at least three immediately adjacent individually addressable regions of all other sets of the package.

3. The titration package of claim 1, wherein the at least three addressable regions of the at least two sets are differentiated from each other by at least one means selected from the following group, or any combination thereof: highlighting by color and/or shading and/or imprint, provision of a blister pack at the position of the addressable region; provision of an indentation/elevation; provision of a different material or a gradient in material, provision of a pouch or other conceivable containment for a pharmaceutical composition.

4. The titration package of claim 1, wherein the pharmaceutical composition is any chemical element, chemical compound, composition, mixture or material that is used or may be used to treat any conceivable illness, disease, medical condition, including food supplements, nutritional supplements or other supplements or agents provided for affecting any conceivable bodily or mental function of human beings or animals.

5. The titration package of claim 1, wherein the pharmaceutical composition is a solid.

6. The titration package of claim 5, wherein the solid is provided as at least one member selected from the following group: tablets, tabloids, pills, troches, lozenges, suppositories, capsules, granules, fine granules, shaped bodies, pellets and beads.

7. The titration package of claim 1, wherein the two different dosages provided in the at least two different sets differ by at least 10%.

8. The titration package of claim 1, wherein three or more different dosages are provided per titration package in three or more different sets.

9. The titration package of claim 8, wherein each set comprises at least five addressable regions.

10. The titration package of claim 1, wherein the at least two sets are present as foldable flaps respectively arranged along one edge of a polygonal central area.

11. The titration package of claim 1, wherein the at least two sets are present as at least two individual sub-packages in the form of polyhedral or polygonal boxes, foldably connected to each other by at least one hinge per two packages.

12. The titration package of claim 1, wherein the fact that the dosages are different between at least two sets is indicated by at least one of the following: imprinting the dosage or any other differentiating feature onto or next to each addressable region and/or on any solid pharmaceutical compound associated therewith; imprinting the dosage or any other differentiating feature next to a set, or part thereof, of addressable regions, color-coding each or some addressable region(s) of a given set and/or color-coding each or any solid pharmaceutical compound associated therewith; associating different dosages with differing shapes of the addressable regions and/or the solid pharmaceutical compounds associated therewith, providing a highlighting bar of different color and/or different shading encompassing two or more addressable regions of one set; providing different blister packages for different sets.

13. The titration package of claim 1, wherein indicia are provided next to each addressable region and/or next to each pharmaceutical composition.

14. The titration package of claim 13, wherein the indicia are consecutive days ranging from "1" to at least "7".

15. The titration package of claim 1, wherein the pharmaceutical composition is a medicament for treating Alzheimer's Disease.

16. The titration package of claim 1, wherein the pharmaceutical composition is or comprises memantine.

17. A kit comprising the titration package of claim 1, memantine or memantine hydrochloride and instructions.

18. The titration package of claim 1, wherein the two different dosages provided in the at least two different sets differ by at least 20%.

19. The titration package of claim 1, wherein the two different dosages provided in the at least two different sets differ by at least 50%.

20. The titration package of claim 1, wherein the two different dosages provided in the at least two different sets differ by at least 100%.

21. The titration package of claim 1, wherein four or more different dosages are provided per titration package in four or more different sets.

22. The titration package of claim 1, wherein the fact that the dosages are different between at least two sets is indicated by a combination of two or more of the following: imprinting the dosage or any other differentiating feature onto or next to each addressable region and/or on any solid pharmaceutical compound associated therewith; imprinting the dosage or any other differentiating feature next to a set, or part thereof, of addressable regions, color-coding each or some addressable region(s) of a given set and/or color -coding each or any solid pharmaceutical compound associated therewith;

associating different dosages with differing shapes of the addressable regions and/or the solid pharmaceutical compounds associated therewith, providing a highlighting bar of different color and/or different shading encompassing two or more addressable regions of one set; providing different blister packages for different sets.

23. The titration package of claim 13, wherein the indicia are consecutive days ranging from "1" to at least "28 ".

24. The titration package of claim 1, wherein the at least two sets are present as at least two individual sub-packages in the form of rectangular boxes, square boxes or parallelepipeds, foldably connected to each other by at least one hinge per two packages.

25. The titration package of claim 8, wherein each set comprises at least seven addressable regions.

* * * * *